United States Patent [19]

Goepp et al.

[11] Patent Number: 4,543,949

[45] Date of Patent: Oct. 1, 1985

[54] CUSTOM VALVED CERVICAL CAP

[75] Inventors: Robert A. Goepp, Chicago; Uwe E. Freese, Oak Park, both of Ill.

[73] Assignee: University Patents, Inc., Westport, Conn.

[21] Appl. No.: 619,037

[22] Filed: Jun. 11, 1984

Related U.S. Application Data

[62] Division of Ser. No. 310,493, Oct. 13, 1981, Pat. No. 4,467,789, which is a division of Ser. No. 108,319, Dec. 31, 1979, Pat. No. 4,322,463.

[51] Int. Cl.⁴ .................................................. A61F 5/46
[52] U.S. Cl. ...................................... 128/127; 128/131
[58] Field of Search ................ 128/127, 128, 131, 130

[56] References Cited

U.S. PATENT DOCUMENTS

| | | | |
|---|---|---|---|
| 3,952,737 | 4/1976 | Lipfert et al. | 128/127 |
| 4,007,249 | 2/1977 | Erb | 128/127 |
| 4,322,463 | 3/1982 | Goepp et al. | 128/131 |
| 4,326,510 | 4/1982 | Buckles | 128/127 |
| 4,363,318 | 12/1982 | Goepp et al. | 128/131 |
| 4,369,219 | 1/1983 | Goepp et al. | 128/127 |
| 4,381,771 | 5/1983 | Gabbay | 128/127 |
| 4,384,572 | 5/1983 | Goepp | 128/131 |
| 4,401,534 | 8/1983 | Goepp et al. | 128/131 |
| 4,450,836 | 5/1984 | Goepp et al. | 128/127 |
| 4,467,789 | 8/1984 | Goepp et al. | 128/127 |

Primary Examiner—Gene Mancene
Assistant Examiner—C. W. Shedd
Attorney, Agent, or Firm—Dressler, Goldsmith, Shore, Sutker & Milnamow

[57] ABSTRACT

A non-invasive birth control device in the form of a custom-formed, valved cervical cap is disclosed. The cervical cap comprises a cup-shaped elastomeric shell substantially complementary with contiguous surface of portio vaginalis cervicis when in contact therewith and having an aperture at the apex of the shell. The aperture is covered by an elastomeric web secured to the shell and defines, together with the shell, a one-way valve means having a discharge port offset from the aperture. The cervical cap can be fabricated from a specially designed blank of a thermoplastic elastomeric material using a replica of cervix uteri as a mold.

21 Claims, 9 Drawing Figures

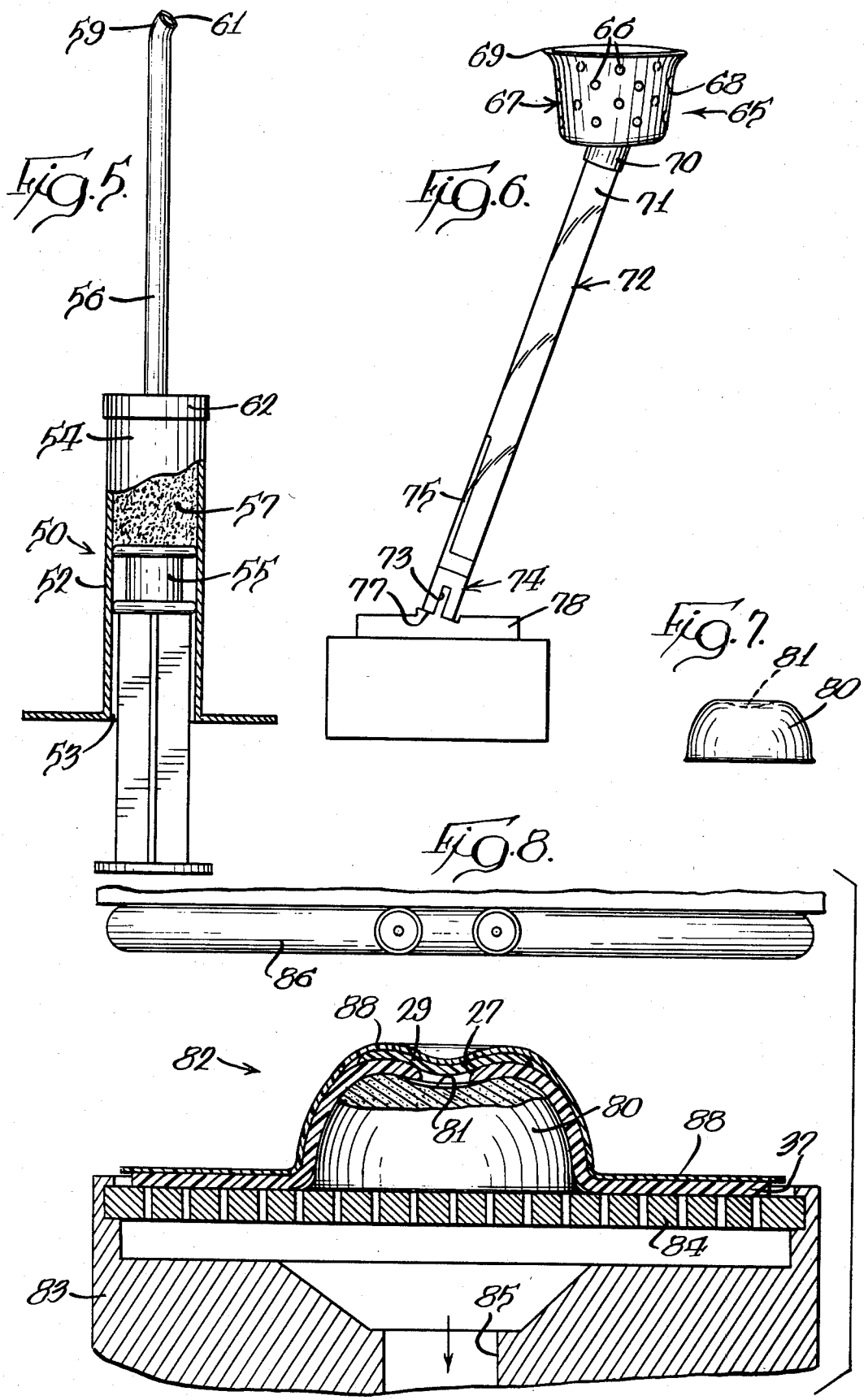

CUSTOM VALVED CERVICAL CAP

This is a division of application Ser. No. 310,493, filed Oct. 13, 1981 now U.S. Pat No. 4,467,789, which application is a division of application Ser. No. 108,319, filed Dec. 31, 1979, now U.S. Pat No. 4,322,463, granted Mar. 30, 1982.

TECHNICAL FIELD

This invention relates to contraceptive devices and means for making such devices.

BACKGROUND OF THE INVENTION

Caps for cervix uteri as a birth control means have been known for a long time and have been found among the artifacts of antiquity. It has been reported that Aetius of Amida suggested for this purpose the use of a pomegranate shell cut into a hollow cup, and that beeswax discs fashioned to fit over the cervix have been used in Europe.

Modern cervical caps comprise a pre-formed rubber cap that is positioned over the cervix uteri to act as a sperm barrier. Such caps are manufactured in several sizes to accommodate the various uterine sizes normally encountered; however, with such caps the fit for a particular individual is inexact and necessarily a compromise. As a result, these caps often become dislodged during coitus and have to be removed periodically to accommodate normal uterine discharges. Thus, such caps are inconvenient to use and have not achieved a high degree of reliability.

Premanufactured cervical caps with valves are also known and are shown in U.S. Pat. No. 2,836,177 to Sells, U.S. Pat. No. 3,952,737 to Lippert et al. and German Pat. No. 475,496 to Leopold. These caps also suffer from the aforementioned lack of stability and are subject to dislodgement during use.

U.S. Pat. No. 4,007,249 to Erb describes a technique for custom fabrication of a cervical cap having a valve that is inserted during manufacture. The manufacturing expedients disclosed in this particular patent contemplate the painting of a liquid, polymerizable elastomeric material onto the cervix uteri followed by the polymerization of the painted material or, in the alternative, the use of a mold which retains a liquid, polymerizable elastomeric material in contact with the exocervical surface until it is polymerized.

The former expedient is impractical because the surface to which the liquid, polymerizable material is applied is wet with mucus and quite slippery, thus the applied material would fall off the exocervical surface due to gravity before polymerization of the material could take place and, in any event, it would be impossible to control the thickness of the applied polymerizable material during in situ polymerization. A cervical cap having a relatively non-uniform thickness is undesirable, however, because it is unstable and is likely to be dislodged in use. The second expedient disclosed in the Erb patent would also produce caps having an undesirable variable cap thickness that is likely to bring about dislodgement.

A further shortcoming of the caps shown in the Erb patent is that the prefabricated valving means utilized are of the leaflet or flap type. In such valves a viscous droplet of cervical mucus could hold the valve in an open position for an undesirably long time period, thereby providing an access aperture for sperm and defeating the very purpose of the cap. Moreover, inasmuch as the polymerizable material of the cap is in a fluid state when it surrounds the prefabricated valve, some of the fluid material may become enmeshed with the valve and interfere with its intended valving action after the material has polymerized.

U.S. Pat. No. 4,007,249 to Erb also mentions a technique disclosed initially by F. A. Wilde in 1838 in *Das Weibliche Gebar-Unvermogen* according to which a cervical cap allegedly can be made from a special wax impression of the vaginal portion of the cervix. As recognized by Erb, such a technique cannot produce an identical, negative-image, cervix-conforming inside surface because the cervix would be deformed while the wax impression is being made. The uterus is suspended in the lower abdomen by ligaments, is easily movable, and would tend to move up into the abdomen even with a gentle force applied to the cervix. As a result, accurate registration would be prevented by such a movement with attendant lack of stability for the cervical cap produced in such manner.

The techniques described by Erb are also likely to suffer from the same drawback, albeit for a different reason. In particular, in practicing these techniques the vaginal wall has to be expanded using a vaginal speculum or similar implement in order to expose the cervix during cap molding. This expedient tends to distort the cervix as well, elongating it along an imaginary line between the tips of the inserted, open vaginal speculum blades and shortening the cervix along an imaginary line at right angles to the imaginary line between the tips of the speculum blades. The attendant cervical distortion exceeds the limits for prosthetic stability of the cervical cap that is produced.

Accordingly, while a stable, well-fitting cervical cap can be an effective birth-control device, heretofore it has not been possible to produce a cervical cap that has the requisite stability against dislodgement and that can be worn for extended periods of time such as months, or even years, without removal.

SUMMARY OF INVENTION

The present invention, in one aspect, contemplates a non-invasive birth control device in the form of a removable cervical cap. The cap is custom made and comprises a form-fitting apertured, elastomeric shell in which the aperture is situated in communication with the external os of cervix uteri when in place and is covered with an elastomeric web conforming and secured to the shell and, together with the shell, defining a one-way valve means having a discharge port offset from the aperture.

A preferred embodiment of the cap includes a cup-shaped elastomeric shell having a convex outer surface and a concave inner surface that is substantially complementary with contiguous surface of portio vaginalis cervicis when in contact therewith. The shell defines an aperture at the apex thereof. An elastomeric web positioned over the aperture conforms and is secured to the outer surface of the shell about the aperture and defines a pocket communicating with the aperture and providing a one-way valve having a discharge port for a uterine discharge while the birth control device is in place. The discharge port of the valve is off-set from the aperture.

The shell of the cap has a depth sufficient to receive a major portion of the portio but the periphery of the shell terminates short of fornices vaginae. Preferably the shell has at least a band of substantially uniform rigidity circumscribing the portio and in contact therewith. More preferably this band of substantially uniform rigidity is a band of substantially uniform shell thickness covering the entire area of the prominent portion of the cervix surrounding the external os thereof, i.e., the cervical eminence around the external os. It is also preferable that the peripheral edge of the shell is feathered, i.e., tapered or beveled from the outer surface of the shell toward the shell periphery.

The birth control device can be conveniently formed from a blank which is a substantially planar sheet of an elastomeric thermoplastic material, preferably having a substantially uniform thickness, provided with a central aperture. The elastomeric web, having a thickness less than the thickness of the planar sheet, is superposed over the aperture and is secured to the planar sheet, usually about the major portion of the aperture periphery, defining a pocket which provides a one-way fluid passageway extending from the aperture, between the web and the sheet, and to a discharge port defined by the sheet and an unsealed or free edge of the web.

The cervical cap contemplated by the present invention can be fabricated by first making an impression of the exocervical surface of cervix uteri in the vagina in a substantially undistorted, relaxed state, making a replica of the protruding portion of cervix uteri, molding the cervical cap utilizing the aforementioned blank, and then trimming away excess material.

Yet another aspect of the present invention contemplates an implement for making the impression of the cervix uteri which comprises, in combination, an impression tray and a syringe having an elongated nozzle received within said tray.

The impression tray includes a hollow cup for receiving the cervix and having a flexible wall that terminates in a peripheral, outwardly flared, anterior lip. The cup is also provided with a bottom aperture. A posterior sleeve, integral with the cup, surrounds the bottom aperture. The tray also includes a hollow, elongated stem the proximal end of which is received within the posterior sleeve. The stem defines a passageway communicating with the cup interior. The length of the stem is such as to facilitate the removal of the vaginal speculum while the tray is held in place.

The syringe includes a hollow body portion, a movable plunger within the body portion, and an elongated nozzle communicating with the hollow body portion and adapted to be received within the passageway defined by the hollow stem of the tray.

To make an impression of the cervix, the impression tray is positioned over the cervix with the stem protruding from the vagina. A physiologically tolerable, hardenable paste is dispensed from the nozzle of the syringe when inserted into the stem. The paste is distributed over the cervix and within the confines of the hollow cup of the tray. The dispensed paste is permitted to harden in situ, and thereafter the tray, containing the fixed cervical impression, is removed from the vagina. A replica of the cervix is then cast from the obtained impression and hardened. Thereafter the cervical cap is produced by positioning the aforementioned blank over the replica, softening the blank by application of heat thereto, and then pressing the heat-softened blank against the replica by vacuum, air pressure, or otherwise. After the surface of the softened blank contiguous with the replica has been deformed to assume a contour substantially complementary to that of the replica, the deformed blank is cooled, removed from the replica, and trimmed to a desired size.

The valved cervical cap embodying the present invention is a non-invasive and entirely passive birth control device. The cap does not interfere with the normal hormonal balance of the individual wearer and thus avoids the side effects commonly encountered with hormonal contraceptives.

Inasmuch as the cap is not placed within a human body like an intrauterine device but, instead, is positioned on the exocervical surface of cervix uteri, it does not have to be sterilized. Likewise, no foreign body reaction and attendant rejection has been encountered.

The cap may be worn for extended periods of time, no preplanning, anticipation, or periodic attention is needed. Thus, there is no interference with the spontaneity of sexual activity. Additionally, the presence of the cap may protect the cervix, uterus and Fallopian tubes from undesirable external influences and infections.

The cap embodying this invention can be fabricated in a relatively short time period, of the order of about five minutes, using a replicated cast of the prospective user's cervix uteri. Little technical skill is required for fabrication.

The one-way valve included in the present cap provides the further advantages of reliability and increased sperm travel distance in the unlikely event that sperm does enter the space between the web and the shell, since the possible sperm entry region is distant from the shell aperture. The normal cyclical changes in the viscosity of cervical mucus do not affect the efficacy or the barrier characteristics of the valve. In contradistinction to the previously known leaflet or flap-type valves which could be held open by a viscous droplet of cervical mucus, the present valve design causes droplet-like cervical mucus descending from the cervical os to flatten out into a very thin film, which does not hold open the valve itself.

BRIEF DESCRIPTION OF THE DRAWINGS

In the drawings,

FIGS. 5 and 6 illustrate devices suitable for practicing the present invention;

FIG. 7 is a side elevational view showing a cast replica of the cervix of a female uterus; and FIG. 8 is an enlarged sectional elevational view illustrating the manufacture of a cervical cap in accordance with the present invention.

DESCRIPTION OF PREFERRED EMBODIMENTS

Figure 1:
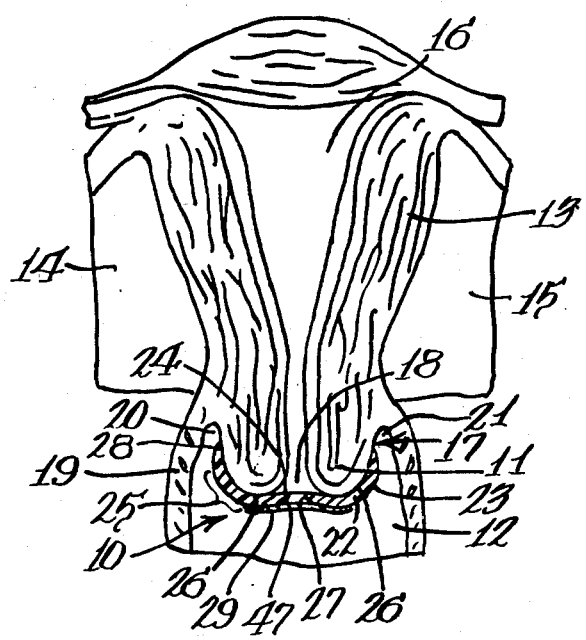
FIG. 1 is an elevational view, partly in section, of a portion of the internal organs of the female reproductive system with a cervical cap embodying the present invention in place.

Referring to FIG. 1, valved cervical cap 10 is shown positioned on exocervical surface 17 of cervix uteri 11, i.e., on the portio vaginalis cervicis or that portion of uterus 13 that protrudes into vagina 12. Uterus 13 is supported by broad ligaments 14 and 15, and defines fundus 16 that terminates in cervical os 18. Vaginal wall 19 and cervix 11 together define the fornices vaginae, i.e., lateral fornices 20 and 21 as well as the anterior and posterior fornices (not shown).

Cap 10 is a cup-shaped elastomeric shell 22 having convex outer surface 23 and concave inner surface 24. Surface 26 of the portio vaginalis cervicis is not distorted by cap 10 and is in mating contact with concave inner surface 24 at least along band 25 of shell 22 which is of substantially uniform rigidity. In the area of contact, concave inner surface 24 is substantially complementary with the contiguous surface 26 of the portio vaginalis cervicis. Preferably the thickness of shell 22 is substantially uniform, at least along peripheral band 25, for optimum stability of cap 10 when in place. Also, it is preferred that the band of substantially uniform thickness constitutes a major portion of shell 22.

Aperture 27 is provided in elastomeric shell 22 at the apex thereof and, as shown in FIG. 1, is positioned adjacent to cervical os 18 when cap 10 is in place. An external cover for aperture 27 is provided by elastomeric web 29 that is integral with shell 22. Web 29 is secured to shell 22 about a major portion of its periphery but also having an unsecured or free edge portion (FIG. 2) that together with adjacent surface portion of convex surface 23 defines a discharge port or external opening 43. Web 29 lies against shell 22 and substantially conforms to the contour thereof. In some instances web 29 may also be under tension and/or biased against convex surface 23. Web 29 and the covered portion of outer surface 23 together define a pocket that communicates with aperture 27 and forms a one-way valve extending from aperture 27, between web 29 and surface 23, and defining discharge port 43 in a direction away from the apex of shell 22, and thus spaced from aperture 27. Preferably the defined discharge port is situated at least about one aperture diameter away from aperture 27, and more preferably, is situated near or at shell periphery 35.

This one-way valve opens under increased uterine pressure and permits the passage of fluids such as mucus, menstrual flow, and the like from fundus 16 to vagina 12 without disturbing the positioning of cervical cap 10 and without permitting the entry of sperm into fundus 16. Additionally, the precise fit of cervical cap 10 onto the portio permits mucus to flow around it; however, at the same time the forces generated by the flow of mucus assist in orienting and in holding cap 10 firmly in place.

Figure 2:
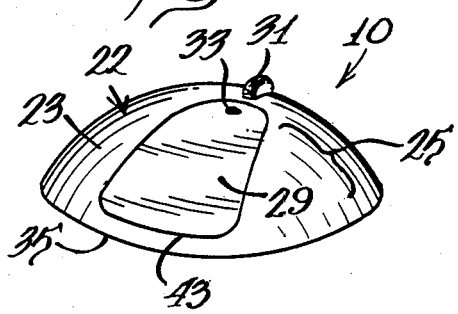
FIG. 2 is an enlarged perspective view of a valved cervical cap embodying the present invention.

As shown in FIG. 2, optionally cap 10 can be provided with an integral tactile orientation marker 31 for the purpose of facilitating orientation of cap 27 upon insertion, as well as enabling the wearer to periodically assure herself that cap 10 remains properly positioned. Visual indicia 33 may also be provided on elastomeric web 29 in some instances for the purpose of facilitating the locating of aperture 27 underneath web 29 during manufacture of cap 10 as will be described in detail hereinbelow.

Shell 22 is dimensioned so as to have a depth sufficient to receive a major portion of the portio as illustrated in FIG. 1; however, periphery 35 of shell 22 terminates short of the fornices vaginae so as to guard against dislodgment of cap 10 during activity that may cause uterus 13 to shift position and/or to deform or distend the normal configuration of the fornices. To avoid dislodgment of the cap during momentary, severe uterine displacement it is important that peripheral edge 35 is sufficiently elastic to remain in contact with the exocervical surface contiguous therewith even during such momentary uterine displacement. For this purpose it is preferable that peripheral edge 35 be feathered, i.e., tapered or beveled as shown in FIG. 1 at 28.

Cap 10 preferably is positioned on cervix uteri 11 so that discharge port or external opening 43 of the valve defined by web 29 in conjunction with convex outer surface 23 is located in or near the posterior fornix and also at a location on surface 23 that is closer to shell periphery 35 than to the apex of the shell. In the embodiment illustrated in FIG. 2 discharge port 43 is substantially coincidental with periphery 35 and preferably is situated no more than about 1 to about 3 millimeters from periphery 35. This results in a manifold increase in the distance that sperm must travel to reach cervical os 18.

A portion of the increased distance for sperm travel is in vagina 12 where the environment is very inhospitable to sperm motility due to the relatively low ambient pH. Usually sperm can survive in the vaginal vault only for a time period of about one to two hours. Inasmuch as sperm can move at a velocity of about one to two millimeters per minute, the substantial increase in the distance that sperm must travel with cap 10 in place alone markedly reduces the likelihood of fertilization. Sperm travel to cervical os 18 via the valve means in cap 10 is possible only in close proximity to the walls defining the valve means. Inasmuch as at least shell 22, and preferably both shell 22 and web 29 are of a thermoplastic elastomeric material, which materials exhibit an inhibitory effect on sperm motility, the likelihood of sperm reaching cervix uteri 11 is further reduced.

Shell 22 can be made of a wide variety of thermoplastic elastomeric materials, the so-called thermoplastic elastomers, such as polyolefin blends, styrene/elastomer block copolymers, copolyesters, and polyurethane block copolymers. While these thermoplastic elastomers differ chemically, their morphology is similar. Blocks or domains of relatively hard thermoplastic constituents link elastomeric constituents in a network that behaves like a chemically crosslinked rubbery structure. At forming temperatures the relatively hard thermoplastic domains of the structure soften and allow the polymeric material to flow. Upon cooling, these relatively hard domains resolidify and re-establish the rubber-like, elastic structure.

Thermoplastic elastomers that exhibit a surface charge provide a further advantage for the present purposes in that the presence of such a charge on the fabricated shell and/or web tends to inhibit sperm motility.

For purposes of the present invention, the shell materials particularly suitable are the styrene/elastomer block copolymers such as those commercially available from the Shell Chemical Company, Oak Brook, Ill., under the designation "Kraton" and "Kraton G" and described in U.S. Pat. No. 3,231,635 to Holden et al. These styrenic thermoplastic elastomers are block copolymers of polystyrene and an elastomer such as polyisoprene, polybutadiene, ethylene-propylene, or ethylenebutylene rubber.

While thermoplastic elastomeric materials of varying hardness may be used to fabricate shell 22, for optimum stability against dislodgment preferably the material should be harder than the cervical tissue that comes in contact therewith, yet the hardness should not be so high as to cause discomfort to the wearer or her consort. Preferably the shell material has a Shore A durometer hardness value of about 35 to about 70, and more preferably of about 45 to about 60.

The shell material can be opaque, semitransparent or transparent; however, for ease of handling or positioning during manufacture of the cervical cap a transparent or clear material is preferred.

Web 29 can be made from the same elastomeric material or from a different elastomeric material, as long as web 29 can be secured to shell 22. For ease of manufacture it is preferred to have web 29 of the same elastomeric material as the shell material but thinner. The shell-to-web thickness ratio usually is about 7:1 to about 3:1 and preferably about 5:1. In a typical cervical cap embodying the present invention the shell thickness is about 1.5 millimeters and the web thickness is about 0.3 to about 0.4 millimeters.

The relative thicknesses of the shell and the integral web in each instance depend on a variety of factors such as the manufacturing procedure, forming temperatures, modulus of elasticity, and the like considerations. In general, however, the web thickness is selected so as to provide a valve-opening pressure of about 10 to about 15 millimeters of mercury for the one-way valve formed by the coaction of web 29 with the outer surface 23 of shell 22 contiguous therewith.

The material for web 29 need not be thermoplastic as long as it exhibits the desired elasticity and can be secured to shell 22. Not only heat sealing or ultrasonic bonding but other bonding means, e.g., adhesive bonding, can be utilized as well. In addition to the aforementioned thermoplastic elastomers, the web portion of the present valved cervical cap can be made from materials such as natural rubber, silicone rubber, polyurethanes, fluorocarbon rubbers, styrene-butadiene rubbers, and the like.

Figure 3:
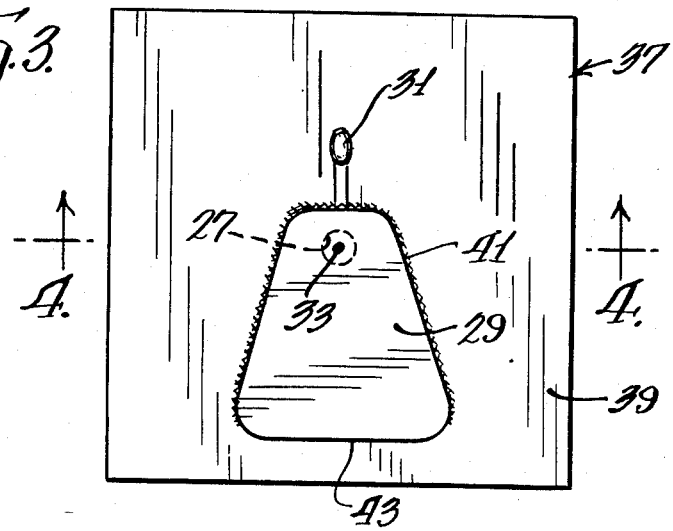
FIG. 3 is a plan view of a blank suitable for fabricating a cervical cap embodying this invention.
Figure 4A:
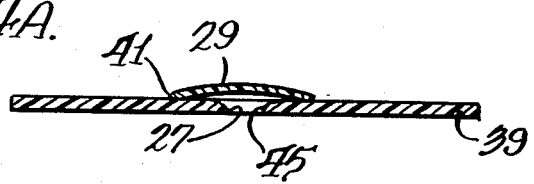
FIG. 4A is a sectional view taken along plane 4—4 in FIG. 3.

Valved cervical cap 10 can be fabricated by molding a blank of the type shown in FIGS. 3 and 4A wherein blank 37 comprises substantially planar sheet 39 of elastomeric material. Aperture 27 in the central region of sheet 39 is covered by elastomeric web 29. The contour of web 29 is not critical and can be generally fan-like, bell-shaped, trapezoidal, or circular, for example, as long as the web substantially conforms to the molded shell after the cap has been fabricated.

Web 29, in turn, is secured to sheet 39, e.g., by bonding peripheral region 41 thereof. The securement of web 29 to sheet 39, and thus ultimately to cap 10, is sufficient to permanently attach web 29 to sheet 39 but provides an unsealed, i.e., free, edge portion which serves to define, in part, external valve opening or discharge port 43. In essence, web 29, when secured to sheet 39, defines a pocket or pockets communicating with underlying aperture 27 and provides a one-way passageway or channel between web 29 and that portion of sheet 39 which ultimately becomes a web-covered portion of the convex outer surface 23 for cap 10, terminating in discharge port 43 that is situated at least one aperture diameter away from aperture 27. Preferably the cross-sectional area of the defined passageway increases with increasing distance from aperture 27 as measured along convex surface 23 of shell 22. Thus, in case of a trapezoidal web, for instance as shown in FIG. 3, the relatively shorter of the two substantially parallel sides of the trapezoid is positioned nearer to aperture 27 than the relatively longer parallel side, and bonded peripheral region 41 extends about the major portion of the periphery of aperture 27. The diameter of aperture 27 is usually about 5 to about 10 millimeters.

Aperture 27 can be a through-aperture with rectangular edges, if desired. However, during fabrication, a relatively thin, thermoplastic, elastomeric web may be drawn or forced into aperture 27 too far and may be excessively deformed or even perforated at the line of contact with a rectangular, sharp edge defining aperture 27. The use of such relatively thin webs, if desired, is facilitated if the aperture-defining edge portion adjacent to web 29 is beveled as at 45 in FIG. 4A or rounded as at 47 in FIG. 1. In this manner the likelihood that web 29 may be perforated or unduly distorted during fabrication is reduced. Tactile orientation marker 31 is positioned adjacent to a sealed juncture of web 29 and sheet 39.

Figure 4B:
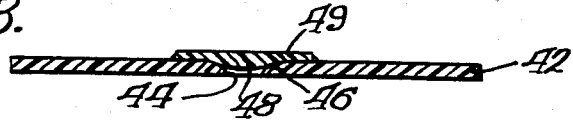
FIG. 4B is a sectional view similar to that in FIG. 4A but showing an alternate cross-sectional configuration for the valve means in a cervical cap of this invention.

An alternate, suitable one-way valve configuration utilizing a relatively thin web is illustrated in FIG. 4B. In this particular embodiment, aperture 44 in thermoplastic elastomeric sheet 42 is covered by web 49 having unitary protuberance 48 extending into aperture 44 and contacting beveled surface 46, i.e., the web 49 is thicker in the region of aperture 44. When a custom, valved cervical cap is fabricated using a cap blank of the type shown in FIG. 4B, protuberance 48 will abut beveled surface 46 and thus will prevent excessive deformation of the web itself during fabrication.

It should be noted, however, that even in the case of a substantially uniformly thick web some deformation into the shell aperture, such as aperture 27 (FIGS. 1, 3 and 8), is not objectionable as long as web integrity is not impaired. Such deformation, as best seen in FIG. 8, also can provide a unitary protuberance that projects into the aperture and enhances the valving action. In addition, the web may be relatively thicker in the region overlying the aperture.

In some instances, particularly when sheet 39 is relatively thick, e.g., of the order of about 2.5 millimeters or more, it is desirable to extend bevel 45 on the aperture edge portion substantially to the juncture 41 of sheet 39 and web 29 so as to provide a substantially uniform thickness throughout. Alternatively, or in addition, the region surrounding aperture 27 and covered by web 29, in the region between juncture 41 and aperture 27 may be countersunk or thinned out for the same purpose.

A prefabricated blank of the type described offers the substantial advantages of ease of custom cap fabrication by a practitioner associated with the practicing physician or with a medical laboratory.

For optimum fit, concave inner surface 24 of cap 22 is substantially complementary with the surface of the portio vaginalis cervicis contiguous therewith. While it is desirable that concave inner surface 24 projects slightly toward cervical os 18 about the periphery of aperture 27, i.e., has local convexity in the aperture region complementary to the concavity of the cervix in the region surrounding cervical os 18, no portion of surface 24 enters cervical os 18. To this end, the cervix in its normal, undistorted configuration is first replicated as a rigid mold, e.g., in plaster, and the obtained replica is then utilized to mold the cervical cap.

Initially an impression of cervix uteri is made using a physiologically tolerable, hardenable paste. Suitable for this purpose is an aqueous paste made from dental impression powder, e.g., using an algin derivative, usually an alginate such as sodium alginate.

The cervical impression can be made utilizing the implements shown in FIGS. 5 and 6. Syringe 50, shown in FIG. 5, includes hollow body portion 52 having an open end 53 and opposed dispensing end 54 that terminates into elongated nozzle 56 in communication with hollow body portion 52. Plunger 55 is positioned within hollow body portion 52 and is adapted to dispense the syringe contents through nozzle 56. Impression paste 57, e.g., aqueous alginate paste, is contained within hollow body portion 52. To facilitate the distribution of impression paste 57 over the cervix during the course of making the impression, it is preferable to have a nozzle the distal end 59 of which is offset from the longitudinal axis of the nozzle itself. In this manner nozzle discharge port 61 is situated in a plane that is at an acute angle, preferably at an angle of about 45 degrees, with respect to the longitudinal axis of nozzle 56, and can dispense impression paste 57 laterally over the cervix in all directions by simply rotating syringe 50. In an alternate manner, nozzle 56 can be rotatably mounted on syringe body 52 by means of nozzle-bearing hub 62 that is rotatable with respect to syringe body 52.

Preparatory to making a cervical impression as contemplated by the present invention, vagina 12 is expanded using a vaginal speculum so as to expose the cervix. Thereafter impression tray 65 (FIG. 6) is inserted through the speculum and into the vagina, and positioned so that hollow cup 67 thereof envelops the cervix. Cup 67 has a flexible, preferably transparent, wall 68 made from an elastomeric material such as silicone rubber, polyurethane, or the like, that terminates in a peripheral, outwardly flared, anterior lip 69 the purpose of which is to keep out adjacent vaginal wall. Wall 68 and lip 69 are also designed so as to trap the cervix and to prevent its upward rotation with attendant closure of the anterior fornix space when the patient is in a supine position while the cervical impression is made.

Flexible wall 68 is further provided with a plurality of spaced perforations such as perforation 66. Cup 67 at the bottom thereof is provided with a bottom aperture surrounded by posterior sleeve 70. Proximal end 71 of hollow, elongated stem 72 is received within sleeve 70. Stem 72 defines a passageway that communicates with the interior of cup 67. A pair of opposed mounting notches, such as notch 73, are provided in distal end 74 of stem 72. Also at or near distal end 74 marker means 75 is provided on stem 72 for indicating a preselected orientation of cup 67.

While cup 67 and stem 72 can be coaxial, for ease of manipulation and insertion during the making of a cervical impression, and also to facilitate the entrapment of the cervix, it is preferred that the longitudinal axes of cup 67 and stem 72 intersect at an included angle of about 15 to about 25 degrees, and more preferably about 20 degrees.

To make a cervical impression once tray 65 is appropriately positioned enveloping the cervix, nozzle 56 is inserted through hollow stem 72. Preferably, length of nozzle 66 is selected so as to extend for substantially the length of stem 72. More preferably distal end 59 projects into cup 67 through the bottom aperture thereof but remains spaced from the cervix. Hub 62 (FIG. 5) on syringe, upon abutting open end 77 of stem 72, provides a positive stop that prevents nozzle aperture 61 from coming in contact with the cervix. In instances where nozzle 56 is longer than stem 72, appropriate stop means can be provided on nozzle 56 itself or within stem 72 at the proximal end 71 received within sleeve 71.

Impression paste 57 is then dispensed from syringe 50 and distributed so as to cover the cervix, and speculum is removed from the vagina without removing tray 65, and the paste permitted to set. The length of stem 72 is selected long enough to permit the easy removal of the speculum without disturbing the position of tray 65. As the impression paste fills cup 67, minor amounts of the paste exude through perforations 66 and, upon setting, anchor the formed impression within tray 65.

After the paste has set, usually within about 90 seconds, tray 65 together with the cervical impression contained therewithin is lifted from the cervix and placed onto vibrating table 78 for casting a replica of the cervix.

The casting operation entails pouring a slurry of plaster of Paris, or like casting material, into tray 65 while the latter is vibrated to permit any trapped air to rise to the surface and to assure that each and every crevice of the formed impression is filled with the slurry. After the slurry has hardened, replica 80 (FIG. 7) is removed from tray 65 and is ready for use in fabricating cervical cap 10.

To this end vacuum molding techniques, e.g., drape forming, can be readily utilized; however, any other molding technique can be utilized as long as the material to be molded can be made to conform closely to the cervical replica, for example, by means of positive air pressure. For purposes of illustration a preferred vacuum molding technique will be described in detail hereinbelow.

Referring to FIG. 8, vacuum molding apparatus 82 comprises base 83 that supports foraminous plate 84 and heat source 86, e.g., a calrod heating element or infrared lamp, in a spaced relationship relative to plate 84. Alternatively, heat can be supplied by a stream of hot air. In the case of a radiant heat source, such as an infrared lamp, the heat-radiating surfaces can be contoured so as to provide a substantially uniform distance between the heat source and the blank portion nearest thereto. Channel 85 in base 83 communicates with a vacuum source (not shown) and permits vacuum to be drawn through plate 84.

Replica 80 is positioned on plate 84 and blank 37 positioned thereover so that visual indicia 33 is superposed over cervical os region 81 of replica 80. A release agent, e.g., an aerosol spray of lecithin commercially available under the designation "Pam" from Boyle-Midway, Inc., New York, N.Y. 10017, is applied to the exposed surface of blank 37, and between the web and the underlying sheet and the blank is then covered with thin protective sheet 88, e.g., a polyethylene terephthalate film, or the like. Preferably sheet 88 is perforated in order to facilitate the vacuum forming operation. Heat source 85 is then turned on and heat applied to sheet 37 until it begins to soften and conform to replica 80 by its own weight. Thereafter the vacuum source is turned on and vacuum drawn through foraminous plate 84 so as to press softened sheet firmly against replica 80. Heat source 86 is then turned off or removed, and the formed sheet is permitted to cool while vacuum is maintained. Once cooled to a permanent contour, sheet 37 is removed from replica 80, and the formed cervical cap is excised therefrom and trimmed to the desired shell depth. The specific shell depth in each instance will depend on the contour of the portio vaginalis cervicis in a given case; however, the shell peripheral edge, i.e., periphery 35, should not extend into the fornices vaginae. The feathering or beveling of shell periphery 35 is usually done during the final trimming operation.

Valved cervical caps embodying the present invention, made from styrene/elastomer block copolymers, and having the general configuration shown in FIG. 2 have been satisfactorily worn by sexuallyactive female volunteers for a cumulative time period in excess of 290 months.

The foregoing disclosure and the accompanying drawings are intended as illustrative and are not to be construed as limiting. Still other variations within the spirit and scope of the present invention as defined by the claims are possible and will readily present themselves to those skilled in the art.

We claim:

1. A non-invasive birth control device which comprises
a cup-shaped elastomeric shell having a convex outer surface and a concave inner surface that is substantially complementary with a contiguous surface of portio vaginalis cervicis in its actual configuration when in contact therewith, said shell defining an aperature at the apex thereof and having a depth sufficient to receive a major portion of said portio, but the periphery of said shell terminating short of fornices vaginae; and
an elastomeric web over said aperture and secured to said outer surface about said aperture defining a passageway communicating with said aperture and providing a discharge port along said convex outer surface and offset from said aperture;
said web conforming to and coacting with a contiguous portion of said convex outer surface to provide a one-way valve means for uterine discharge entering said aperture from within said shell.

2. The birth control device in accordance claim 1 wherein said shell and said web are of the same elastomeric material.

3. The birth control device in accordance with claim 2 wherein the elastomeric material is a styrene/elastomer block copolymer.

4. The birth control device in accordance with claim 1 wherein said shell has a Shore A durometer hardness value of about 35 to about 70.

5. The birth control device in accordance with claim 1 wherein said shell has a Short A durometer hardness value of about 45 to about 60.

6. The birth control device in accordance with claim 1 wherein at least portion of said shell in contact with the contiguous surface of portio vaginalis cervicis defines a band of substantially uniform thickness.

7. The birth control device in accordance with claim 1 wherein the average thickness ratio of said shell to said web is about 5:1, respectively.

8. The birth control device in accordance with claim 1 wherein said elastomeric web has a fan-like configuration and is contiguous with said convex outer surface.

9. The birth control device in accordance with claim 1 wherein said one-way valve means is adapted to open at a fluid pressure of about 10 to about 15 millimeters of mercury.

10. The birth control device in accordance with claim 1 wherein said shell is substantially transparent.

11. The birth control device in accordance with claim 1 wherein said shell is provided with a tactile marker near the apex of said shell.

12. The birth control device in accordance with claim 1 wherein said web is in tension.

13. The birth control device in accordance with claim 1 wherein said shell has a thickness of about 1.5 to about 2 millimeters.

14. The birth control device in accordance with claim 1 wherein said web has a thickness of about 0.3 to about 0.4 millimeters.

15. The birth control device in accordance with claim 1 wherein said web is positioned over said aperture so that the web portion directly over the aperture protrudes therein.

16. The birth control device in accordance with claim 1 wherein a peripheral band of said shell having a substantially uniform thickness constitutes a major portion of said shell.

17. The birth control device in accordance with claim 1 wherein said discharge port is situated at a distance of at least about an aperture diameter away from said aperture.

18. The birth control device in accordance with claim 1 wherein said discharge port is situated near the periphery of said shell.

19. The birth control device in accordance with claim 1 wherein the periphery of said shell is feathered.

20. The birth control device in accordance with claim 1 wherein said web has a unitary protuberance extending into said aperture.

21. The birth control device in accordance with claim 1 wherein said web is thicker in the region of said aperture.

* * * * *